United States Patent

Hardy et al.

[11] 3,970,636
[45] July 20, 1976

[54] TETRAMETHYLPIPERIDINYLPHOSPHINE OXIDES AS LIGHT STABILIZERS FOR POLYMERS

[75] Inventors: William Baptist Hardy, Bound Brook; Peter Vincent Susi, Middlesex, both of N.J.

[73] Assignee: American Cyanamid Company, Stamford, Conn.

[22] Filed: Apr. 15, 1975

[21] Appl. No.: 568,331

[52] U.S. Cl. .................. 260/45.8 NE; 260/293.51; 260/293.88; 260/293.9
[51] Int. Cl.² .................. C08K 5/50; C07D 211/44; C07D 211/94
[58] Field of Search .............. 260/45.8 NE, 293.51, 260/293.88, 293.9

[56] References Cited
UNITED STATES PATENTS

| | | | |
|---|---|---|---|
| 3,003,996 | 10/1961 | Newland et al. | 260/45.9 |
| 3,338,910 | 8/1967 | Kuhnis et al. | 260/294.3 |
| 3,341,625 | 9/1967 | Gillham et al. | 260/887 |
| 3,734,883 | 5/1973 | Holt | 260/45.8 |
| 3,759,926 | 9/1973 | Chalmers et al. | 260/293.9 |
| 3,850,877 | 11/1974 | Cook | 260/45.8 |
| 3,875,169 | 4/1975 | Ramey et al. | 260/293.54 |

*Primary Examiner*—Lewis T. Jacobs
*Assistant Examiner*—R. A. White
*Attorney, Agent, or Firm*—Philip Mintz

[57] ABSTRACT

Compounds of the formula:

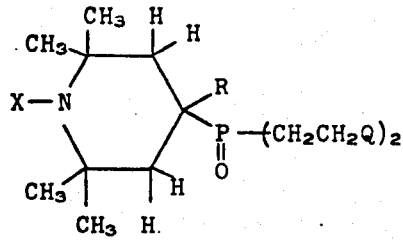

wherein X is —H, —OH, or —O.; R is —H or —OH; and Q is —C≡N or

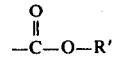

where R' is alkyl of 1 to 18 carbon atoms or hydrogen are useful for stabilizing polymers against degradation by ultraviolet radiation.

17 Claims, No Drawings

TETRAMETHYLPIPERIDINYLPHOSPHINE OXIDES AS LIGHT STABILIZERS FOR POLYMERS

This invention relates to certain novel compounds and to their use as light stabilizers for polymers. More particularly, this invention relates to compounds of the formula (I):

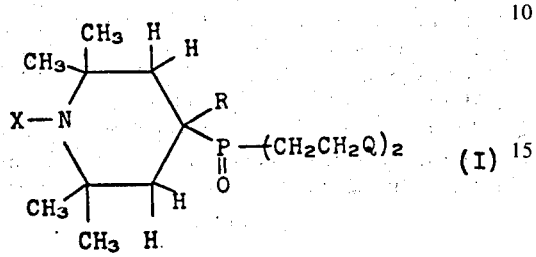

wherein X is —H, —OH, or —O·; R is —H or —OH; and Q is —C≡N or

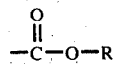

where R' is alkyl of 1 to 18 carbon atoms or hydrogen and to the use of such compounds to stabilize polymers, particularly polyolefins such as polypropylene, against degradation by ultraviolet radiation.

It is well known that sunlight and other sources of ultraviolet radiation cause degradation of polymers as evidenced by embrittlement or yellowing of plastic articles made therefrom. It is also well known that this degradation can be inhibited by use of ultraviolet light stabilizers incorporated in or on such articles. Continuing efforts are being made to discover ever better ultraviolet light stabilizers which will be superior to those currently available.

In accordance with the present invention, we have discovered that the above-described compounds provide effective stabilization of polymers against deterioration by ultraviolet radiation.

Plastic materials which are stabilized against degradation by ultraviolet light using these compounds include polyvinyl chloride, polyvinylidene chloride, copolymers of vinyl chloride and vinylidene chloride, polystyrene, polyesters, cellulose acetate, polyvinyl acetate, polyvinyl fluoride, polymethyl methacrylate, polyurethanes, polycarbonates and natural and synthetic rubbers such as polymers of acrylonitrile, butadiene, and styrene. They are particularly useful in polyolefins, such as polyethylene and polypropylene. These compounds may be incorporated in or on such plastic materials by any of the various standard procedures known in the art for such purpose, such as by dry blending the additive with the polymer in powder or granular form followed by molding or extruding; by milling; by immersing the polymer as film, sheet, fibers, etc. in a solution of the additive in an appropriate solvent (as in a dye process); etc.

The plastic material should contain an effective stabilizing amount of the compound of formula (I), which amount will depend on the nature of the plastic and the amount of exposure to ultraviolet light to which the plastic will be subjected. Generally, an amount between about 0.1% and 5% by weight of plastic will be found satisfactory and between about 0.2% and 2% will be preferred.

The compound of formula (I) may be used in the plastic alone or in combination with other additives, such as fillers, antioxidants, flame retardants, heat stabilizers, anti-slipping and anti-static agents, supplemental light stabilizers, pigments, dyes, lubricants, etc.

The compounds of formula (I) can be prepared in several ways. In one procedure, a 4-keto-piperidine compound of formula (II) is reacted with a phosphine oxide of formula (III) to yield the desired product of formula (I) as illustrated by the following reaction:

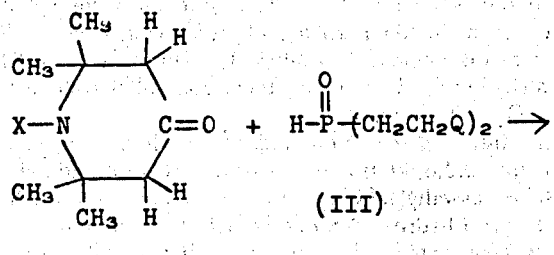

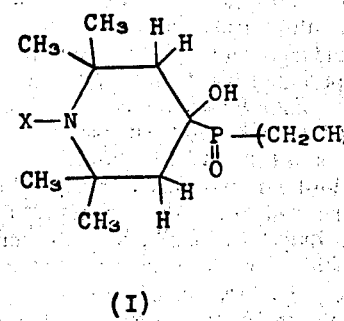

In another procedure, a 4-keto-piperidine compound of formula (II) is reacted with a phosphine of formula (IV) in concentrated hydrochloric acid to yield the desired product of formula (I) as illustrated by the following reaction:

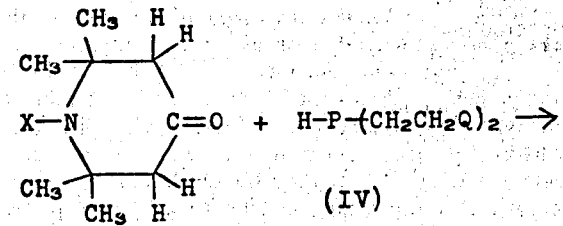

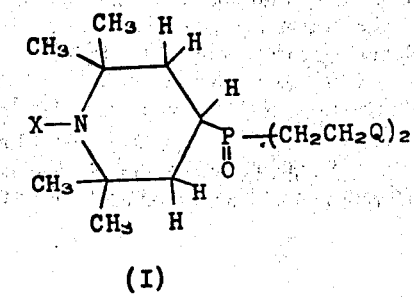

In this procedure, if Q is —C≡N in reactant compound (IV), under these strongly acid conditions, the Q in the product (I) will be

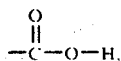

which can be esterified with a suitable alcohol.

In the foregoing reactions, compounds of formula (II) are known compounds, disclosed in U.S. Pat. No. 3,759,926. The above compounds of formula (I) wherein X is —O· can be obtained by oxidizing those compounds wherein X is —H with an oxidizing agent such as hydrogen peroxide or perbenzoic acid. The above compounds of formula (I) wherein X is —OH can be obtained by reducing those compounds where X is —O· with hydrogen.

Illustrative of the compounds represented by formula (I) are (2,2,6,6-tetramethyl-4-hydroxy-4-piperidinyl)-bis(2-cyanoethyl)phosphine oxide; (2,2,6,6-tetramethyl-1-oxyl-4-hydroxy-4-piperidinyl)bis(2-cyanoethyl)-phosphine oxide; (2,2,6,6-tetramethyl-1,4-dihydroxy-4-piperidinyl)bis(2-cyanoethyl)phosphine oxide; (2,2,6,6-tetramethyl-4-piperidinyl)bis(2-carboxyethyl)phosphine oxide; (2,2,6,6-tetramethyl-4-piperidinyl)bis(2-carbalkoxyethyl)phosphine oxide where "-alk-" is an alkyl group of 1 to 18 carbon atoms, such as -meth-, -eth-, -prop-, -but-, -hex-, -oct-, -decyl-, -dodecyl-, -octadecyl-, etc.; (2,2,6,6-tetramethyl-1,4-dihydroxy-4-piperidinyl)bis(2-carboxyethyl)phosphine oxide; (2,2,6,6-tetramethyl-1,4-dihydroxy-4-piperidinyl)bis(2-carbalkoxyethyl)phosphine oxide where "-alk-" is as described above; (2,2,6,6-tetramethyl-1-oxyl-4-hydroxy-4-piperidinyl)bis(2-carboxyethyl)phosphine oxide; (2,2,6,6-tetramethyl-1-oxyl-4-hydroxy-4-piperidinyl)bis(2-carbalkoxyethyl)phosphine oxide where "-alk-" is as described above; etc.

As mentioned previously, the compounds of formula (I) may be used in the plastic alone or in combination with other additives, such as fillers, antioxidants, flame retardants, heat stabilizers, anti-slipping and anti-static agents, supplemental light stabilizers, pigments, dyes, lubricants, etc. Such additional additives may be used in the range of 0.2 to 2.0 percent by weight on weight of plastic.

Illustrative of suitable antioxidants are those of the hindered-phenol type, such as 2,6-di-t-butyl-p-cresol; 4,4'-bis(2,6-di-t-butylphenol); 4,4'-bis(2,6-di-isopropylphenol); 2,4,6-tri-t-butylphenol; 2,2'-thiobis(4-methyl-6-t-butylphenol); octadecyl 2(3',5'-di-t-butyl-4'hydroxyphenyl)propionate; etc.; esters of thiodipropionic acid, such as dilauryl thiodipropionate and distearyl thiodipropionate, etc.; hydrocarbyl phosphites, such as triphenyl phosphite, trinonyl phosphite, diphenyldecyl phosphite, etc.; and combinations thereof.

Illustrative of the supplemental light stabilizers are those of the benzotriazole class, such as 2-(2'-hydroxy-5'-methylphenyl)benzotriazole; 2-(2'-hydroxy-3',5'-di-butylphenyl)-5-chlorobenzotriazole; those of the hydroxybenzophenone type, such as 2-hydroxy-4-methoxybenzophenone; 2-hydroxy-4-octyloxybenzophenone; 2,2'-dihydroxy-4,4'-dimethoxybenzophenone; hindered phenol esters, such as 2', 4'-di-t-butyl-phenyl 3,5-di-t-butyl-4-hydroxybenzoate; metal complexes, such as nickel complexes of 2,2'-thiobis(4-t-octylphenol); nickel butylamine complex of 2,2'-thiobis(4-t-octylphenol); nickel complexes of bis(4-t-octylphenyl)sulfone; nickel dibutyl dithiocarbamate; nickel salts of 4-hydroxy-3,5-di-t-butylbenzyl phosphonic acid monoalkyl esters where alkyl is methyl, ethyl, propyl, butyl, etc.; nickel complex of 2-hydroxy-4-methylphenyl-undecyl ketone oxime; etc. Further illustrative examples of suitable antioxidants and of suitable supplemental light stabilizers can be found in columns 3 and 4 of U.S. Pat. No. 3,488,290 and 3,496,134 and the other patents mentioned therein.

The following examples, in which parts and percentages are by weight unless otherwise stated, are presented to further illustrate the present invention.

EXAMPLE 1

Preparation of (2,2,6,6-tetramethyl-4-hydroxy-4-piperidinyl)bis(2-cyanoethyl)phosphine oxide To 100 milliliters of isopropanol was added 8.65 grams (0.05 mole) of 2,2,6,6-tetramethyl-4-piperidone hydrate; 7.81 grams (0.05 mole) of bis(2-cyanoethyl)-phosphine oxide; and 1 gram of triethylamine as catalyst. The reaction mixture was refluxed four hours, cooled in an ice bath, and the crystalline product filtered off. After recrystallization, there was obtained 10.0 grams of white crystalline product of 128°–130°C. melting point, representing a 65% yield.

EXAMPLE 2

Testing in Polypropylene

The compound of Example 1 (0.2% by weight) was dry blended with a mastermix of unstabilized polypropylene (Profax 6401) and 0.2% by weight of a processing antioxidant, 2,4,6-tri-t-butylphenol. The blend was milled for five minutes at 350°–370°F. and the milled sample was compression molded into a film 4–5 mils thick at 400°F. The compression molded film, and a control film identically prepared except without the compound of Example 1, were exposed in a Xenon Weather-O-Meter (Atlas) until they failed. The samples were considered as having failed when the carbonyl content in the infrared spectrum reached 0.1%, a generally accepted point of film embrittlement. The test sample lasted 1000 hours, appreciably longer than the control which only lasted 500–800 hours.

EXAMPLE 3

Preparation of (2,2,6,6-tetramethyl-4-hydroxy-1-oxyl-4-piperidinyl)-bis(2-cyanoethyl)phosphine oxide To 100 milliliters of isopropanol was added 12 grams (0.0707 mole) of 2,2,6,6-tetramethyl-4-piperidone-1-oxyl; 11 grams (0.0707 mole) of bis(2-cyanoethyl)-phosphine oxide; and 2 grams of triethylamine as catalyst. The reaction mixture was refluxed for one and one-half hours during which time an orange solid was produced, cooled to room temperature, and filtered to remove the solid product. The crude product (14.0 grams) was recrystallized from acetonitrile to obtain 4.9 grams of orange crystals of 170°–171°C. melting point, representing a 21% yield. On testing by the procedure of Example 2, the polypropylene test sample containing 0.2% by weight of this compound lasted 2100 hours, much longer than the control which only lasted 500–800 hours.

EXAMPLE 4

Preparation of (2,2,6,6-tetramethyl-4-piperidinyl)bis(2-carbethoxyethyl)phosphine oxide To 50 milliliters of concentrated hydrochloric acid was added, with cooling, 13 grams (0.075 mole) of 2,2,6,6-tetramethyl-4-piperidone hydrate, after which 10.5 grams (0.075 mole) of bis(2-cyanoethyl)phosphine was added under a nitrogen atmosphere. The mixture was heated at reflux for twenty-four hours, then evaporated to obtain a viscous liquid, which was then dissolved in 100 milliliters of absolute ethanol. Then 100 milliliters of benzene was added and the mixture boiled to collect the azeotrope in a Dean-Stark trap and remove the water formed during esterification. When no more water came off, the solution was filtered and evaporated to an oil. The oil was dissolved in a 10% aqueous sodium carbonate solution and extracted with chloroform. The chloroform layer was washed with dilute aqueous sodium carbonate, then dried over sodium sulfate, then stripped to obtain 26 grams of a pale orange oil, representing an 89% yield of the desired compound. On testing by the procedure of Example 2, the polypropylene test sample containing 0.2% by weight of this compound lasted 1800 hours, much longer than the control which only lasted 500–800 hours.

EXAMPLE 5

Preparation of (2,2,6,6-tetramethyl-4-piperidinyl)bis(2-carboctoxyethyl)phosphine oxide The procedure of Example 4 was followed except that 100 milliliters of concentrated hydrochloric acid, 26 grams (0.15 mole) of 2,2,6,6-tetramethyl-4-piperidone hydrate, and 21 grams (0.15 mole) of bis(2-cyanoethyl)phosphine were used in the initial reaction and 100 milliliters of n-octanol and 200 milliliters of benzene were used in the esterification step. After azeotropic distillation to remove the water and filtering the remaining reaction mixture to remove the insoluble ammonium chloride by-product, most of the excess n-octanol was removed by vacuum distillation. The residue was dissolved in petroleum ether and filtered to remove residual ammonium chloride. The petroleum ether solution was washed with 10% aqueous sodium carbonate solution to liberate the free base of the desired product, however, extensive emulsification occurs. After extended standing, the organic layer was separated, washed with water, dried and evaporated to give 48 grams of clear liquid consisting of 75% by weight of the desired product and 25% by weight of n-octanol. On testing by the procedure of Example 2, the polypropylene test sample containing 0.2% by weight of this compound lasted 1600 hours, much longer than the control which only lasted 500–800 hours.

EXAMPLE 6

Preparation of (2,2,6,6-tetramethyl-1,4-dihydroxy-4-piperidinyl)-bis(2-cyanoethyl)phosphine oxide The procedure of Example 1 is used except 0.05 mole of 2,2,6,6-tetramethyl-1-hydroxy-4-piperidone is used instead of the 2,2,6,6-tetramethyl-4-piperidone.

EXAMPLE 7

Preparation of (2,2,6,6-tetramethyl-4-hydroxy-4-piperidinyl)bis(2-carbethoxyethyl)phosphine oxide The procedure of Example 1 is used except that 12.51 grams (0.05 mole) of bis(2-carbethoxyethyl)phosphine oxide is used instead of the bis(2-cyanoethyl)phosphine oxide.

EXAMPLE 8

Preparation of (2,2,6,6-tetramethyl-4-hydroxy-4-piperidinyl)bis(2-carboctadecyloxyethyl)phosphine oxide The procedure of Example 1 is used except that 52.4 grams (0.075 mole) of bis(2-carboctadecyloxyethyl)phosphine oxide is used instead of the bis(2-cyanoethyl)phosphine oxide.

EXAMPLE 9

Preparation of (2,2,6,6-tetramethyl-4-piperidinyl)bis(2-carboctadecyloxyethyl)phosphine oxide The procedure of Example 5 is used except that 200 milliliters of n-octadecyl alcohol and 200 milliliters of benzene are used in the esterification step.

We claim:
1. A compound of the formula:

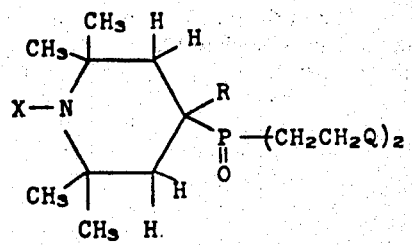

wherein X is —H, —OH, or —O·; R is —H or —OH; and Q is —C≡N or

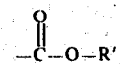

where R' is alkyl of 1 to 18 carbon atoms or hydrogen.
2. A compound as defined in claim 1 wherein Q is —C≡N.
3. A compound as defined in claim 1 wherein Q is

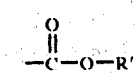

where R' is alkyl of 1 to 18 carbon atoms or hydrogen.

4. A compound as defined in claim 1 which is (2,2,6,6-tetramethyl-4-hydroxy-4-piperidinyl)bis(2-cyanoethyl)phosphine oxide.

5. A compound as defined in claim 1 which is (2,2,6,6-tetramethyl-4-hydroxy-1-oxyl-4-piperidinyl)bis(2-cyanoethyl)phosphine oxide.

6. A compound as defined in claim 1 which is (2,2,6,6-tetramethyl-4-piperidinyl)bis(2-carbethoxyethyl)phosphine oxide.

7. A compound as defined in claim 1 which is (2,2,6,6-tetramethyl-4-piperidinyl)bis(2-carboctoxyethyl)phosphine oxide.

8. A compound as defined in claim 1 which is (2,2,6,6-tetramethyl-1,4-dihydroxy-4-piperidinyl)bis(2-cyanoethyl)phosphine oxide.

9. A compound as defined in claim 1 which is (2,2,6,6-tetramethyl-4-hydroxy-4-piperidinyl)bis(2-carbethoxyethyl)phosphine oxide.

10. A compound as defined in claim 1 which is (2,2,6,6-tetramethyl-4-hydroxy-4-piperidinyl)bis(2-carboctadecyloxyethyl)phosphine oxide.

11. A compound as defined in claim 1 which is (2,2,6,6-tetramethyl-4-piperidinyl)bis(2-carboctadecyloxyethyl)phosphine oxide.

12. A polymer composition containing an amount of a compound as defined in claim 1 effective to stabilize said polymer against degradation by ultraviolet radiation.

13. A composition as defined in claim 12 wherein said polymer is a polyolefin.

14. A composition as defined in claim 13 wherein said polyolefin is polypropylene.

15. A composition as defined in claim 12 wherein said effective amount is about 0.1% to about 5% by weight of said compound on weight of polymer.

16. A composition as defined in claim 12 wherein Q is —C≡N.

17. A composition as defined in claim 12 wherein Q is

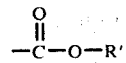

where R' is alkyl of 1 to 18 carbon atoms or hydrogen.

* * * * *